(12) United States Patent
Hares et al.

(10) Patent No.: US 11,903,668 B2
(45) Date of Patent: *Feb. 20, 2024

(54) TORQUE SENSING IN A SURGICAL ROBOTIC WRIST (71) Applicant: CMR SURGICAL LIMITED, Cambridge (GB)

(72) Inventors: Luke David Ronald Hares, Cambridge (GB); Keith Marshall, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 332 days.

This patent is subject to a terminal disclaimer.

(21) Appl. No.: 17/345,218

(22) Filed: Jun. 11, 2021

(65) Prior Publication Data
US 2021/0298858 A1 Sep. 30, 2021

Related U.S. Application Data (63) Continuation of application No. 16/228,852, filed on Dec. 21, 2018, now Pat. No. 11,291,516, which is a (Continued)

(30) Foreign Application Priority Data

May 14, 2015 (GB) ...................................... 1508260

(51) Int. Cl.
A61B 34/00 (2016.01)
B25J 9/16 (2006.01)
(Continued)

(52) U.S. Cl.
CPC ............. A61B 34/76 (2016.02); A61B 34/30 (2016.02); A61B 34/35 (2016.02); B25J 9/1689 (2013.01);
(Continued)

(58) Field of Classification Search
CPC .... B25J 9/1689; B25J 13/085; B25J 17/0275; A61B 2090/066
See application file for complete search history.

(56) References Cited

U.S. PATENT DOCUMENTS 4,805,477 A 2/1989 Akeel
4,911,033 A 3/1990 Rosheim et al.
(Continued)

FOREIGN PATENT DOCUMENTS

CN 101927498 A 12/2010
CN 102186396 A 9/2011
(Continued)

OTHER PUBLICATIONS

Indian Examination Report from corresponding Indian Application No. 202018053666 dated Jan. 12, 2022.
(Continued)

Primary Examiner — Phong Son H Dang
(74) Attorney, Agent, or Firm — Lando & Anastasi, LLP (57) ABSTRACT A surgical robotic component comprising an articulated terminal portion, the terminal portion comprising: a distal segment having an attachment connected thereto, an intermediate segment, and a basal segment whereby the terminal portion is attached to the remainder of the surgical robotic component. The terminal portion further comprises a first articulation between the distal segment and the intermediate segment, the first articulation permitting relative rotation of the distal segment and the intermediate segment about a first axis, and a second articulation between the intermediate segment and the basal segment, the second articulation permitting relative rotation of the intermediate segment and the basal segment about a second axis. The intermediate segment comprises: a third articulation permitting relative rotation of the distal segment and the basal segment about third and fourth axes, a first torque sensor configured to
(Continued)

sense torque about the third axis, and a second torque sensor configured to sense torque about the fourth axis. The first, second and third articulations are arranged such that in at least one configuration of the third articulation the first and second axes are parallel and the third and fourth axes are transverse to the first axis.

18 Claims, 4 Drawing Sheets

Related U.S. Application Data continuation of application No. 15/153,934, filed on May 13, 2016, now Pat. No. 10,206,752.

(51) Int. Cl.
| | |
|---|---|
| B25J 17/02 | (2006.01) |
| A61B 34/30 | (2016.01) |
| A61B 34/35 | (2016.01) |
| B25J 13/08 | (2006.01) |
| A61B 90/00 | (2016.01) |

(52) U.S. Cl.
CPC ......... *B25J 13/085* (2013.01); *B25J 17/0275* (2013.01); *A61B 2034/305* (2016.02); *A61B 2090/066* (2016.02)

(56) References Cited

U.S. PATENT DOCUMENTS

| | | | |
|---|---|---|---|
| 5,239,883 | A | 8/1993 | Rosheim |
| 5,428,713 | A | 6/1995 | Matsumaru |
| 5,697,256 | A | 12/1997 | Matteo |
| 5,740,699 | A | 4/1998 | Ballantyne et al. |
| 5,828,813 | A | 10/1998 | Ohm |
| 5,855,583 | A | 1/1999 | Wang et al. |
| 6,417,638 | B1 | 7/2002 | Guy et al. |
| 6,676,684 | B1 | 1/2004 | Morley et al. |
| 6,699,177 | B1 | 3/2004 | Wang et al. |
| 6,785,572 | B2 | 8/2004 | Yanof et al. |
| 6,985,133 | B1 | 1/2006 | Rodomista et al. |
| 7,206,626 | B2 | 4/2007 | Quaid, III |
| 7,646,161 | B2 | 1/2010 | Albu-Schaffer et al. |
| 8,182,470 | B2 | 5/2012 | Devengenzo et al. |
| 9,119,653 | B2 | 9/2015 | Amat Girbau et al. |
| 9,317,032 | B2* | 4/2016 | Finkemeyer ......... G05B 19/414 |
| 9,743,936 | B2 | 8/2017 | Huet et al. |
| 10,206,752 | B2 | 2/2019 | Hares et al. |
| 2003/0100892 | A1 | 5/2003 | Morley et al. |
| 2003/0167061 | A1 | 9/2003 | Schlegel et al. |
| 2004/0024311 | A1 | 2/2004 | Quaid |
| 2004/0106916 | A1 | 6/2004 | Quaid et al. |
| 2004/0106916 | A1 | 6/2004 | Quaid et al. |
| 2007/0120512 | A1 | 5/2007 | Albu-Schaffer et al. |
| 2007/0120512 | A1 | 5/2007 | Albu-Schaffer et al. |
| 2007/0151391 | A1 | 7/2007 | Larkin et al. |
| 2007/0151391 | A1 | 7/2007 | Larkin et al. |
| 2008/0196533 | A1 | 8/2008 | Bergamasco et al. |
| 2010/0292707 | A1 | 11/2010 | Ortmaier et al. |
| 2010/0292707 | A1 | 11/2010 | Ortmaier et al. |
| 2011/0087238 | A1 | 4/2011 | Wang et al. |
| 2011/0144659 | A1 | 6/2011 | Sholev |
| 2011/0172823 | A1 | 7/2011 | Kim et al. |
| 2011/0172823 | A1 | 7/2011 | Kim et al. |
| 2011/0257786 | A1 | 10/2011 | Caron L'Ecuyer et al. |
| 2011/0257786 | A1 | 10/2011 | Caron L'Ecuyer et al. |
| 2013/0053866 | A1 | 2/2013 | Leung et al. |
| 2013/0131695 | A1 | 5/2013 | Scarfogliero et al. |
| 2014/0005662 | A1 | 1/2014 | Shelton, IV |
| 2014/0276933 | A1 | 9/2014 | Hart et al. |
| 2014/0276933 | A1 | 9/2014 | Hart et al. |
| 2014/0371762 | A1 | 12/2014 | Farritor et al. |
| 2014/0371762 | A1 | 12/2014 | Farritor et al. |
| 2015/0018840 | A1 | 1/2015 | Monfaredi et al. |
| 2015/0018840 | A1 | 1/2015 | Monfaredi et al. |
| 2015/0081098 | A1 | 3/2015 | Kogan |
| 2015/0081098 | A1 | 3/2015 | Kogan |
| 2015/0100066 | A1 | 4/2015 | Kostrzewski et al. |
| 2015/0100066 | A1 | 4/2015 | Kostrzewski et al. |
| 2015/0104283 | A1 | 4/2015 | Nogami et al. |
| 2015/0202015 | A1 | 7/2015 | Elhawary et al. |
| 2015/0257838 | A1 | 9/2015 | Huet et al. |
| 2015/0265358 | A1 | 9/2015 | Bowling et al. |
| 2016/0129588 | A1* | 5/2016 | Pfaff ..................... B25J 9/06 901/4 |
| 2017/0079731 | A1 | 3/2017 | Griffiths et al. |
| 2017/0196644 | A1 | 7/2017 | Elhawary et al. |
| 2018/0021096 | A1 | 1/2018 | Kostrzewski et al. |

FOREIGN PATENT DOCUMENTS

| | | |
|---|---|---|
| CN | 202146362 U | 2/2012 |
| CN | 102892363 | 1/2013 |
| CN | 102892363 A | 1/2013 |
| CN | 104057465 A | 9/2014 |
| CN | 106102630 A | 11/2016 |
| CN | 107666875 A | 2/2018 |
| CN | 110680504 A | 1/2020 |
| EP | 2252231 | 11/2010 |
| EP | 2252231 A2 | 11/2010 |
| GB | 2523224 A | 8/2015 |
| JP | H04502584 A | 5/1992 |
| JP | H07032286 A | 2/1995 |
| JP | 2000505328 A | 5/2000 |
| JP | 2001145634 A | 5/2001 |
| JP | 2009165504 A | 7/2009 |
| JP | 2010155335 A | 7/2010 |
| JP | 2011530373 A | 12/2011 |
| JP | 2012527276 A | 11/2012 |
| JP | 201394920 A | 5/2013 |
| JP | 6465365 B2 | 2/2019 |
| WO | 0203878 A1 | 1/2002 |
| WO | 2009114613 | 9/2009 |
| WO | 2009114613 A2 | 9/2009 |
| WO | 2010007837 A1 | 1/2010 |
| WO | 2010055745 A1 | 5/2010 |
| WO | 2010140844 A2 | 12/2010 |
| WO | 20120007014 A1 | 1/2012 |
| WO | 2013154157 A1 | 10/2013 |
| WO | 20140152418 A1 | 9/2014 |

OTHER PUBLICATIONS

Indian Examination Report from corresponding Indian Application No. 202018053666 dated Jan. 12, 2022.
Indian Examination Report from corresponding Indian Application No. 202018053666 dated Jan. 12, 2022.
Chinese First Notification of Office Action from corresponding Chinese Application No. 202011071694.X dated Oct. 25, 2023.

* cited by examiner

TORQUE SENSING IN A SURGICAL ROBOTIC WRIST

CROSS-REFERENCE TO RELATED APPLICATION

This application is a continuation of U.S. patent application Ser. No. 16/228,852, filed Dec. 21, 2018, titled TORQUE SENSING IN A SURGICAL ROBOTIC WRIST, which is a continuation of U.S. patent application Ser. No. 15/153,934, filed May 13, 2016 [now U.S. Pat. No. 10,206, 752], titled TORQUE SENSING IN A SURGICAL ROBOTIC WRIST, which claims the benefit under 35 U.S.C. § 119 of United Kingdom Patent Application No. GB1508260.5 filed on May 14, 2015. Each application referenced above is hereby incorporated by reference herein in its entirety for all purposes.

BACKGROUND

This invention relates to robots for performing surgical tasks.

Various designs of robot have been proposed for performing or assisting in surgery. However, many robot designs suffer from problems that make them unsuitable for performing a wide range of surgical procedures. A common reason for this is that in order for a surgical robot to work well in a wide range of surgical situations it must successfully balance a set of demands that are particular to the surgical environment.

Normally a surgical robot has a robot arm, with a surgical instrument attached to the distal end of the robot arm.

Figure 1:
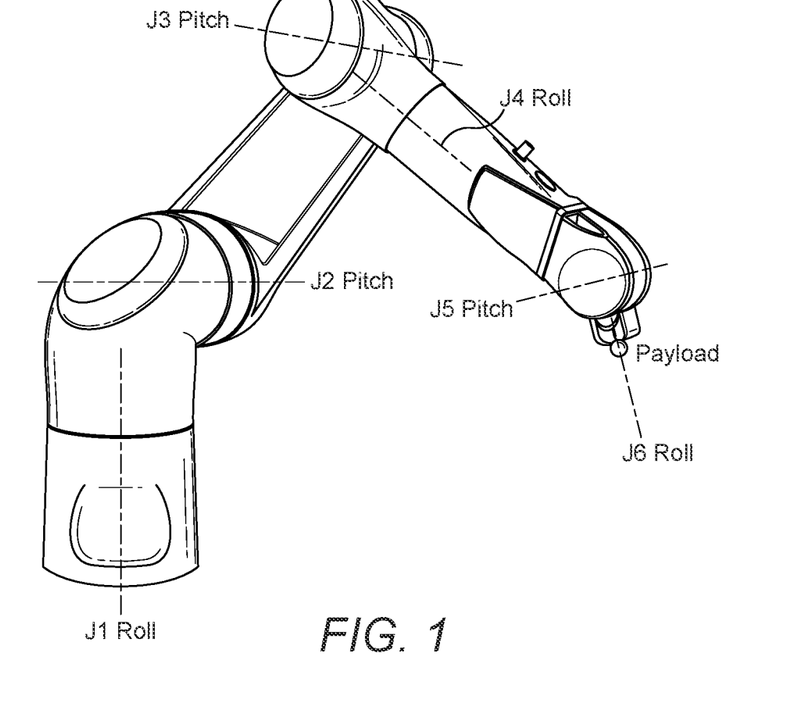
FIG. 1 shows a prior art robot arm.

A common demand on a surgical robot is that its robot arm should offer sufficient mechanical flexibility to be able to position the surgical instrument in a wide range of locations and orientations so that the working tip of the surgical instrument (the end effector) can reach a range of desired surgical sites. This demand alone could easily be met by a conventional fully flexible robot arm with six degrees of freedom, as illustrated in FIG. 1. However, secondly, a surgical robot must also be capable of positioning its arm such that the end effector of the instrument is positioned very accurately without the robot being excessively large or heavy. This requirement arises because unlike the large-scale robots that are used for many other tasks, (a) surgical robots need to work safely in close proximity to humans: not just the patient, but typically also surgical staff such as anaesthetists and surgical assistants, and (b) in order to perform many laparoscopic procedures it is necessary to bring multiple end effectors together in close proximity, so it is desirable for surgical robot arms to be small enough that they can fit closely together. Another problem with the robot of FIG. 1 is that in some surgical environments there is not sufficient space to be able to locate the base of the robot in a convenient location near the operating site.

Figure 2:
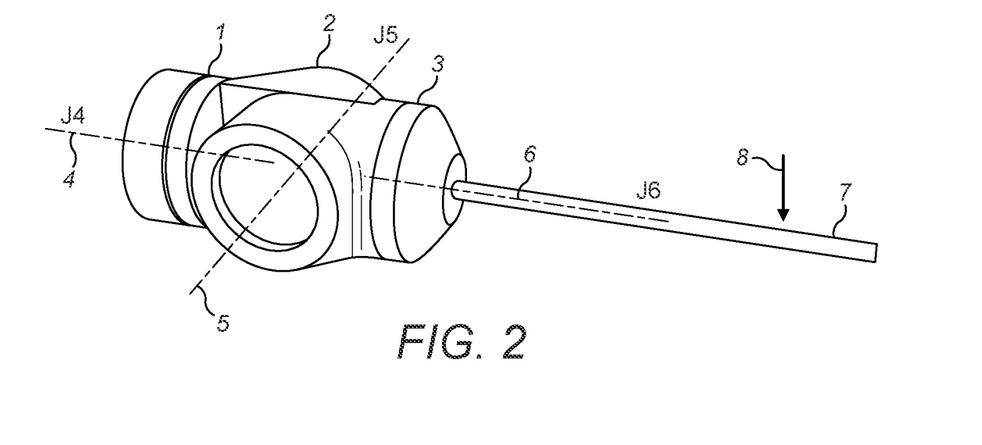
FIG. 2 shows a prior art robot wrist.

Many robots have a wrist (i.e. the terminal articulated structure of the arm) which comprises two joints that permit rotation about an axis generally along the arm ("roll joints") and between them one joint that permits rotation about an axis generally transverse to the arm (a "pitch joint"). Such a wrist is shown in FIG. 2, where the roll joints are indicated as 1 and 3 and the pitch joint is indicated as 2. With the wrist in the configuration shown in FIG. 2 the axes of the joints 1 to 3 are indicated as 4 to 6 respectively. This wrist gives an instrument 7 the freedom of movement to occupy a hemisphere whose base is centred on axis 4. However, this wrist is not well suited for use in a surgical robot. One reason for this is that when the pitch joint 2 is offset by just a small angle from the straight position shown in FIG. 2 a large rotation of joint 1 is needed to produce some relatively small lateral movements of the tip of the instrument. In this condition, when the pitch joint is almost straight, in order to move the end effector smoothly in a reasonable period of time the drive to joint 1 must be capable of very fast operation. This requirement is not readily compatible with making the arm small and lightweight because it calls for a relatively large drive motor and a sufficiently stiff arm that the motor can react against it without jolting the position of the arm.

Another common demand on a surgical robot is that it should be designed such that forces which are applied to the surgical instrument are measurable. Because the surgeon is not directly in contact with the surgical instrument during robotic surgery, tactile feedback is lost compared to manual surgery. This lack of tactile sensation means that the surgeon does not know how much force is being applied when using the surgical instrument. This affects the surgeon's dexterity. Additionally, too much exerted force can cause internal damage to the patient at the surgical site, and can also damage the surgical instrument and the robot arm. By measuring the forces applied to the surgical instrument, these can be implemented in a force feedback mechanism to provide force feedback to the surgeon. For example, haptic technology can be used to convert the measured forces into physical sensations in the input devices that the surgeon interacts with, thereby providing a replacement for the tactile sensation of manual surgery.

The wrist shown in FIG. 2 enables some force measurement. Specifically, forces which are exerted vertically on the surgical instrument (i.e. perpendicular to axis 5) illustrated by arrow 8, can be measured using a torque sensor applied to the pitch joint 2. However, forces which are applied to the surgical instrument from other directions cannot be sensed using torque sensors applied to the wrist. Other techniques are possible to detect forces applied from other directions, for example by using strain gauges. However, these other techniques require more sensors to be applied to the robot, and hence more electronics are required to route and process the data, which increases the weight and power requirements of the robot.

SUMMARY OF THE INVENTION

According to one aspect of the invention, there is provided a surgical robotic component comprising an articulated terminal portion, the terminal portion comprising: a distal segment having an attachment connected thereto; an intermediate segment; a basal segment whereby the terminal portion is attached to the remainder of the surgical robotic component; a first articulation between the distal segment and the intermediate segment, the first articulation permitting relative rotation of the distal segment and the intermediate segment about a first axis; a second articulation between the intermediate segment and the basal segment, the second articulation permitting relative rotation of the intermediate segment and the basal segment about a second axis; wherein: the intermediate segment comprises: a third articulation permitting relative rotation of the distal segment and the basal segment about third and fourth axes; a first torque sensor for sensing torque about the third axis; and a second torque sensor for sensing torque about the fourth axis; and the first, second and third articulations are arranged such that in at least one configuration of the third articulation the first and second axes are parallel and the third and fourth axes are transverse to the first axis.

The terminal portion may further comprise a third torque sensor for sensing torque about the first axis. The terminal portion may further comprise a fourth torque sensor for sensing torque about the second axis.

Suitably, in the said configuration, the third and fourth axes are transverse to each other. Suitably, in the said configuration, the third and fourth axes are perpendicular to each other. In the said configuration the third and fourth axes may be perpendicular to the first axis. In the said configuration, the first and second axes may be collinear.

The third and fourth axes may intersect each other.

The first articulation may be a revolute joint. The second articulation may be a revolute joint. The third articulation may be a spherical joint or a pair of revolute joints. The third articulation may be a universal joint.

Suitably, the only means of articulating the attachment relative to the basal segment are the first, second and third articulations.

The attachment may be located on the first axis.

Suitably, the surgical robotic component is located at the end of a surgical robot arm, and a surgical instrument is attached to the attachment. The surgical instrument may extend in a direction substantially along the first axis.

Alternatively, the surgical robotic component is located at the end of a surgical instrument, and a surgical end effector is attached to the attachment. The surgical end effector may extend in a direction substantially along the first axis.

BRIEF DESCRIPTION OF THE DRAWINGS

The present invention will now be described by way of example with reference to the accompanying drawings. In the drawings.

DETAILED DESCRIPTION

Figure 3:
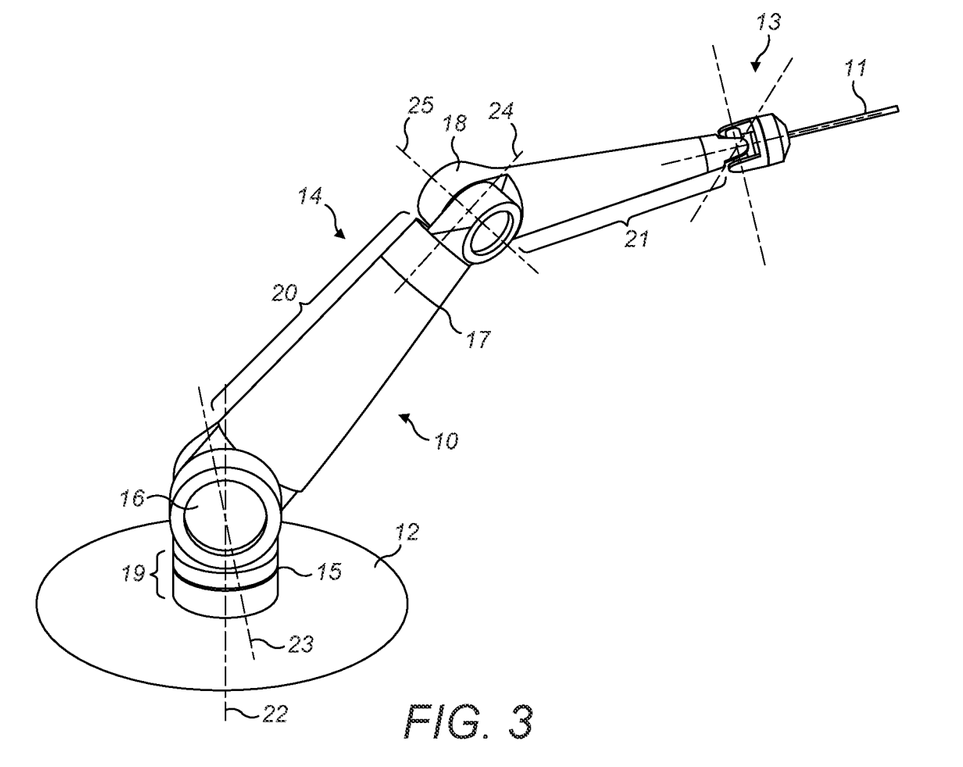
FIG. 3 shows a robot arm according to an embodiment of the present invention having a surgical instrument attached thereto.

The surgical robot arm of FIG. 3 has a wrist in which two joints that permit rotation about axes generally transverse to the distal portion of the arm are located between two joints that permit rotation about axes generally parallel to the distal portion of the arm. This arrangement permits the instrument to move in a hemispherical space whose base is centred on the distal part of the arm, but without requiring high-speed motion of one of the joints in order to move the end effector smoothly, and without requiring motion of any of the other parts of the arm.

In more detail, FIG. 3 shows a robot arm (indicated generally at 10) having a surgical instrument 11 attached thereto. The robot arm extends from a base 12. The base could be mounted to the floor of an operating theatre, or to a fixed plinth, could be part of a mobile trolley or cart, could be mounted to a bed or could be mounted to the ceiling of an operating room. The base is fixed in place relative to the patient's bed or chair when an operation is being carried out.

The robot arm comprises a wrist portion shown generally at 13 and a main portion shown generally at 14. The main portion makes up the majority of the extent of the arm and terminates at its distal end in its attachment to the wrist portion.

The proximal end of the main portion is attached to the base. The wrist portion makes up the distal part of the arm and is attached to the distal end of the main portion.

The main portion of the arm comprises four joints 15, 16, 17, 18 and three shaft sections 19, 20, 21. The joints are revolute joints. The shaft sections are rigid, with the exception of joints 15 and 17 which are set into shaft sections 19 and 20 respectively. Each shaft section may have substantial length, and serve to provide the arm with reach and the ability to offset the wrist laterally and/or vertically from the base. The first shaft section could be truncated relative to the second and third shaft sections if the base is located in a suitable place; particularly if the base is elevated from the floor.

The first shaft section 19 is attached to the base 12. In practice the first shaft section can conveniently extend in a generally upright direction from the base but it could extend at a significant incline to vertical, or even horizontally.

Joint 15 is located in the first shaft section. Joint 15 permits relative rotation of the proximal part of the first shaft section, which is fixed to the base, and the remainder of the arm about an axis 22. Conveniently, axis 22 is parallel with or substantially parallel with the main extent of the first shaft section in forming the arm, which runs from the base towards joint 16. Thus, conveniently the angle of axis 22 to the main extent of the first shaft section in forming the arm could be less than 30°, less than 20° or less than 10°. Axis 22 could be vertical or substantially vertical. Axis 22 could extend between the base and joint 16.

Joint 16 is located at the distal end of the first shaft section 19. Joint 16 permits relative rotation of the first shaft section 19 and the second shaft section 20, which is attached to the distal end of joint 16, about an axis 23 which is transverse to the first shaft section 19 and/or the second shaft section 20. Conveniently axis 23 is perpendicular or substantially perpendicular to either or both of the first and second shaft sections. Thus, conveniently the angle of axis 23 to the main extents of either or both of the first and second shaft sections could be greater than 60°, greater than 70° or greater than 80°. Conveniently axis 23 is perpendicular or substantially perpendicular to axis 22 and/or to the axis 24 to be described below.

Joint 17 is located in the second shaft section. Joint 17 permits relative rotation of the proximal part of the second shaft section and the remainder of the arm about an axis 24. Conveniently, axis 24 is parallel with or substantially parallel with the main extent of the second shaft section. Thus, conveniently the angle of axis 24 to the main extent of the second shaft section could be less than 30°, less than 20° or less than 10°. Axis 24 could intersect or substantially intersect (e.g. within 50 mm of) axis 23 and the axis 25 that will be described below. In FIG. 3 joint 17 is shown located closer to the distal end of the second shaft section than the proximal end. This is advantageous because it reduces the mass that needs to be rotated at joint 17, but joint 17 could be located at any point on the second shaft section. The second shaft section is conveniently longer than the first shaft section.

Joint 18 is located at the distal end of the second shaft section 20. Joint 18 permits relative rotation of the second shaft section and the third shaft section 21, which is attached to the distal end of joint 18, about an axis 25 which is transverse to the second shaft section 20 and/or the third shaft section 21. Conveniently axis 25 is perpendicular or substantially perpendicular to either or both of the second and third shaft sections. Thus, conveniently the angle of axis 25 to the main extents of either or both of the second and third shaft sections could be greater than 60°, greater than 70° or greater than 80°. Conveniently axis 25 is perpendicular or substantially perpendicular to axis 24 and/or to the axis 29 to be described below.

In summary, then, in one example the main portion of the arm can be composed as follows, in order from the base to the distal end of the main portion:
1. a first shaft section 19 having substantial or insubstantial length and containing a joint 15 that permits rotation e.g. about an axis generally along the extent (if any) of the first shaft section in forming the arm (a "roll joint");
2. a joint 16 permitting rotation transverse to the first shaft section and/or to the axis of the preceding joint (joint 15) and/or to the axis of the succeeding joint (joint 17) (a "pitch joint");
3. a second shaft section 20 having substantial length and containing a joint 17 that permits rotation about an axis generally along the extent of the second shaft section and/or to the axis of the preceding joint (joint 16) and/or to the succeeding joint (joint 18) (a roll joint);
4. a joint 18 permitting rotation transverse to the second shaft section and or to the preceding joint (joint 17) and/or to the succeeding joint (joint 28) (a pitch joint); and
5. a third shaft section 21 having substantial length.

Figure 4A:
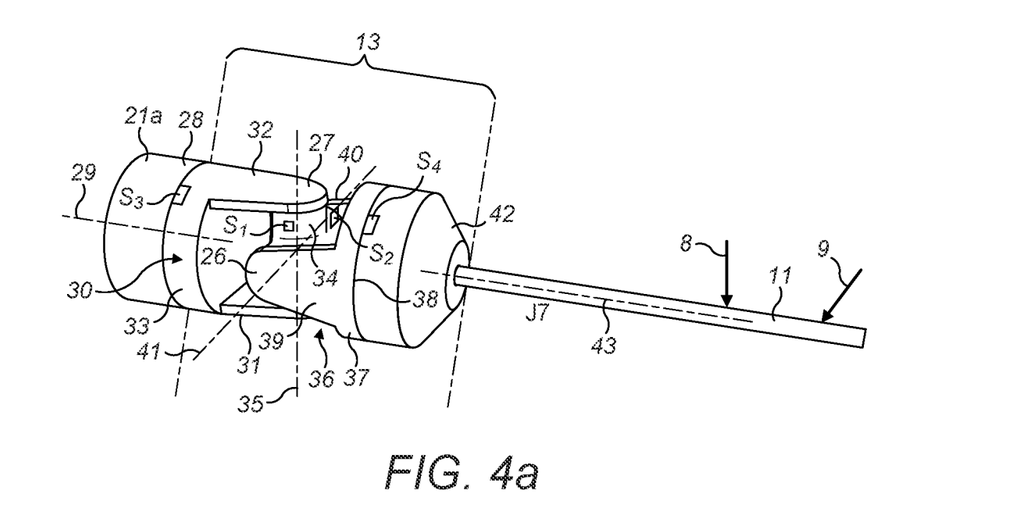
FIG. 4a shows a surgical wrist in a straight configuration.
Figure 4B:
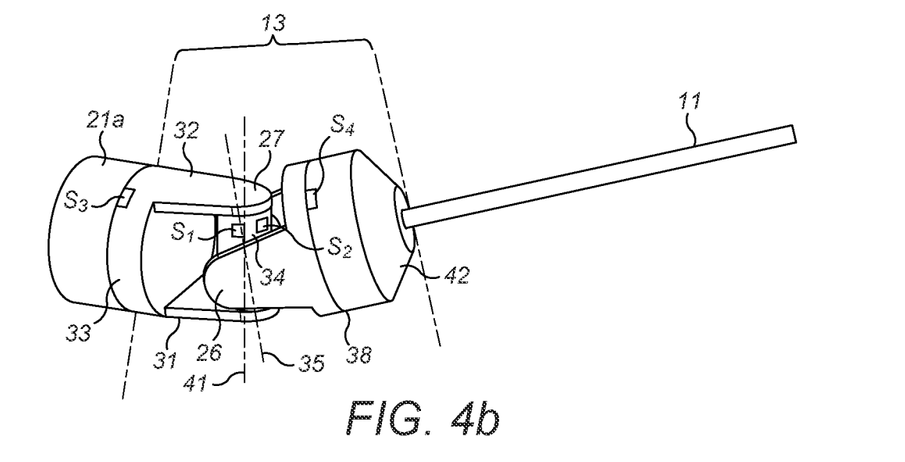
FIG. 4b shows a surgical wrist in a bent configuration.
Figure 4C:
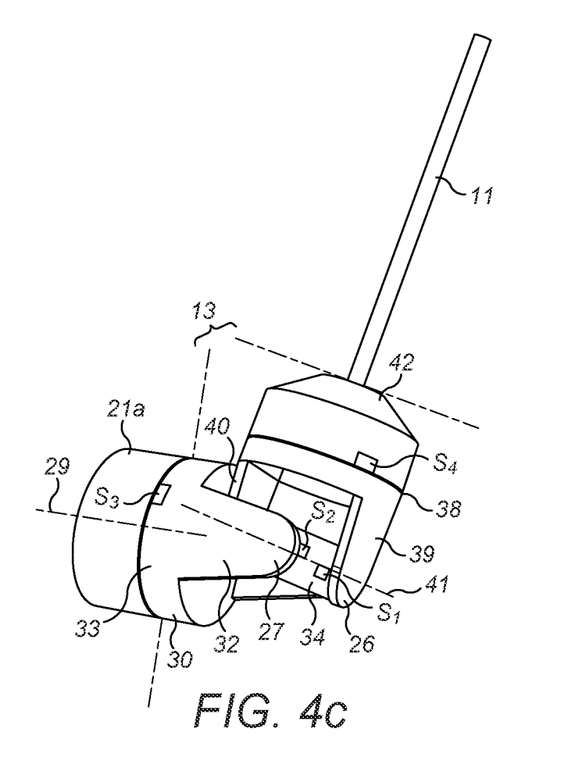
FIG. 4c shows a surgical wrist in a bent configuration.

The wrist portion 13 is attached to the distal end of the third shaft section. FIGS. 4a, 4b, and 4c illustrate a surgical wrist, such as the wrist portion 13 of FIG. 1, in more detail. FIG. 4a shows the wrist in a straight configuration, 4b shows the wrist in a bent configuration from movement at a joint 26, and FIG. 4c shows the wrist in a bent configuration from movement at joints 26, 27 and 28. The straight configuration represents the mid-point of the motions of the transverse joints (26, 27) of the wrist.

The wrist is designated 13 in FIGS. 4a, 4b, and 4c. FIGS. 4a, 4b, and 4c illustrate an example in which the wrist is implemented in the robot arm of FIG. 3. In this implementation, the distal part of the third shaft section is designated 21a in FIGS. 4a, 4b, and 4c. The wrist is attached to the distal end of the third shaft section by a joint 28. Joint 28 is a revolute joint which permits the wrist to rotate relative to the distal end of the arm about an axis 29. Conveniently, axis 29 is parallel with or substantially parallel with the main extent of the third shaft section. Thus, conveniently the angle of axis 29 to the main extent of the third shaft section could be less than 30°, less than 20° or less than 10°. Axis 29 could intersect or substantially intersect (e.g. within 50 mm) axis 25. Axis 29 is conveniently transverse to axis 25.

In an alternative implementation, the wrist 13 is implemented in a surgical instrument. The wrist is implemented in the distal end of the surgical instrument. The proximal end of the surgical instrument is attached to the robot arm. In this implementation, the wrist is attached to the shaft of the surgical instrument by joint 28. As above, joint 28 is a revolute joint which permits the wrist to rotate relative to the instrument shaft about an axis 29. Conveniently, axis 29 is parallel with or substantially parallel with the main extent of the instrument shaft. Thus, conveniently the angle of axis 29 to the main extent of the instrument shaft could be less than 30°, less than 20° or less than 10°.

The proximal end of the wrist is constituted by a wrist base block 30. The wrist base block 30 is attached to joint 28. Wrist base block 30 abuts the distal end of the third shaft section 21 in the case that the wrist is attached to the robot arm of FIG. 3. Alternatively, the wrist base block 30 abuts the distal end of the instrument shaft in the case that the wrist is attached to the surgical instrument. The wrist base block is rigid and comprises a base 33, by which it is attached to joint 28. The wrist base block also comprises a pair of spaced apart arms 31, 32 which extend from the base 33 of the wrist base block in a direction away from the third shaft section 21a or instrument shaft to which the wrist base block is attached. An intermediate member 34 is pivotally suspended between the arms 31, 32 in such a way that it can rotate relative to the arms 31, 32 about an axis 35. This constitutes a revolute joint 27 of the wrist. The intermediate member 34 is conveniently in the form of a rigid block which may be of cruciform shape. A wrist head block 36 is attached to the intermediate member 34. The wrist head block is rigid and comprises a head 37 by which it is attached to a joint 38 to be described below, and a pair of spaced apart arms 39, 40 which extend from the head 37 towards the intermediate member 34. The arms 39, 40 embrace the intermediate member 34 and are attached pivotally to it in such a way that the wrist head block can rotate relative to the intermediate member about an axis 41. This provides revolute joint 26 of the wrist. Axes 35 and 41 are offset from each other at a substantial angle. Axes 35 and 41 are conveniently transverse to each other, and most conveniently orthogonal to each other. Axes 35 and 41 can conveniently intersect or substantially intersect (e.g. within 50 mm). However, the intermediate member could have some extent so that those axes are offset longitudinally. Axes 35 and 29 are conveniently transverse to each other, and most conveniently orthogonal to each other. Axes 35 and 29 can conveniently intersect or substantially intersect (e.g. within 50 mm). Axes 35 and 29 can conveniently intersect axis 41 at a single point, or the three axes may substantially intersect at a single point (e.g. by all intersecting a sphere of radius 50 mm).

In this way the wrist base block, intermediate member and wrist head block together form a universal joint. The universal joint permits the wrist head block to face any direction in a hemisphere whose base is perpendicular to the axis 29 of joint 28. The linkage between the wrist base block and the wrist head block could be constituted by other types of mechanical linkage, for example by a ball joint or a constant velocity joint. Preferably that linkage acts generally as a spherical joint, although it need not permit relative axial rotation of the wrist base block and the wrist head block since such motion is accommodated by joints 28 and 38. Alternatively, joints 26, 27 and 28 could be considered collectively to form a spherical joint. That spherical joint could be provided as a ball joint.

A terminal unit 42 is attached to the head 37 of the wrist head block by revolute joint 38. Joint 38 permits the terminal unit to rotate relative to the head block about an axis 43. Axes 43 and 41 are conveniently transverse to each other, and most conveniently orthogonal to each other. Axes 35 and 29 can conveniently intersect or substantially intersect (e.g. within 50 mm). Axes 35 and 29 can conveniently intersect axis 41 at a single point, or the three axes may substantially intersect at a single point (e.g. by all intersecting a sphere of radius 50 mm).

Wrist 13 also comprises a series of torque sensors, $S_1$, $S_2$, $S_3$ and $S_4$. Each torque sensor is associated with a joint, and senses applied torque about the joint's rotation axis. $S_1$ is associated with joint 27 and senses torque about axis 35. $S_2$ is associated with joint 26 and senses torque about axis 41. $S_3$ is associated with joint 28 and senses torque about axis 29. $S_4$ is associated with joint 38 and senses torque about axis 43. The outputs of the torque sensors are passed to a control unit (not shown) where they form the inputs to a processor (not shown). The processor may also receive inputs from the motors driving the sensed joints. The processor thereby resolves the torque applied to the joints due to motion driven by the motors and the torque applied to the joints due to external forces. All of the torque sensors $S_1$, $S_2$, $S_3$ and $S_4$ may be applied to the wrist 13. Alternatively, $S_3$ and/or $S_4$ may be omitted.

In the implementation in which the wrist is at the distal end of the robot arm of FIG. 3, the terminal unit 42 has a connector such as a socket or clip to which surgical instrument 11 can be attached. This surgical instrument is shown in more detail in FIG. 5. The instrument comprises in instrument base 50, an elongate instrument shaft 51, optionally one or more joints 52 and an end effector 53. The end effector could, for example, be a gripper, a pair of shears, a camera, a laser or a knife. The instrument base and the connector of the terminal unit 42 are designed cooperatively so that the instrument base can be releasably attached to the connector with the shaft extending away from the instrument base. Conveniently the shaft extends away from the instrument base in a direction that is transverse to the axis of joint 26 and/or parallel or substantially parallel and/or coaxial or substantially coaxial with axis 43 of joint 38. This means that the end effector has substantial range of movement by virtue of the joints of the wrist, and that the joints of the wrist can be used conveniently to position the end effector. For example, with the elongation of the instrument shaft running along axis 43, joint 38 can be used purely to orientate the end effector without moving part or all of the instrument shaft 51 with a lateral component in a way that could result in disruption to the tissue of a patient through which the shaft has been inserted to reach an operation site. The fact that the elongation of the instrument shaft extends away from the wrist as described above means that the wrist has a degree of articulation that is similar to the wrist of a human surgeon. One result of that is that many surgical techniques practised by humans can readily be translated to motions of this robot arm. This can help reduce the need to devise robot-specific versions of known surgical procedures. The shaft is conveniently formed as a substantially linear, rigid rod.

In the description above, the length of the wrist base block 30 is less than that of the final shaft section 21 of the robot arm. This is advantageous because it reduces the mass that needs to be rotated at joint 28. However, joint 28 could be located closer to joint 25 than to joints 26 and 27.

Figure 6:
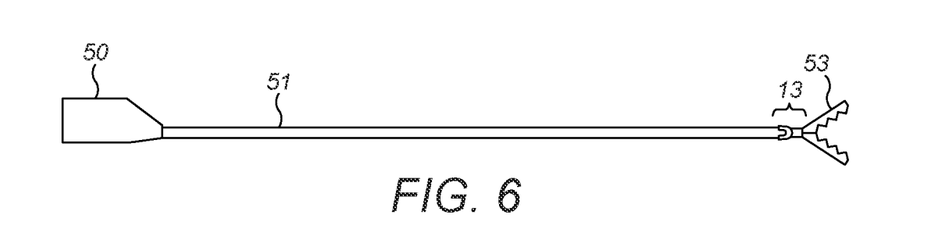
FIG. 6 shows a further surgical instrument.

In the implementation in which the wrist is at the distal end of the surgical instrument, the terminal unit 42 is connected to an end effector 53. This surgical instrument is shown in more detail in FIG. 6. The instrument comprises an instrument base 50, an elongate instrument shaft 51, the wrist 13 and an end effector 53. The end effector may be any of the forms mentioned above. The end effector 53 and the terminal unit 42 are designed such that motion is transferable through the terminal unit 42 to the end effector 53. The joints of the end effector may be driven by motive means in the robot arm to which the instrument is connected. The motion may be transmitted to the joints through cables or linkages in the robot arm and instrument.

It will be appreciated that the wrist of FIGS. 4a, 4b, and 4c has a kinematic redundancy. The end effector 53 could be placed in a wide range of locations in a hemisphere about axis 29 merely by motion of joints 28 and 27. However, it has been found that the addition of joint 26 greatly improves the operation of the robot for surgical purposes by eliminating the kinematic singularity that results from joint pair 28, 27 alone. The addition of joint 26 also simplifies the mechanism of moving the end effector within the patient so that multiple robot arms can work more closely with each other, as will be described in more detail below.

Referring to FIG. 4a in the case that the wrist 13 is at the distal end of a robot arm, when a force 8 is applied vertically to the surgical instrument (i.e. perpendicular to axis 41), this causes rotation of the wrist about axis 41. More specifically, the resolved component of a force applied in the direction 8 causes rotation of the wrist about axis 41. Torque sensor $S_2$ senses this torque, and outputs the sensed torque to the processor. When a force 9 is applied laterally to the surgical instrument (i.e. perpendicular to axis 35), this causes rotation of the wrist about axis 35. More specifically, the resolved component of a force applied in a direction 9 causes rotation of the wrist about axis 35. Torque sensor $S_1$ senses this torque, and outputs the sensed torque to the processor. Thus, loads applied to the surgical instrument are measured by the wrist. Typically, a force applied to the surgical instrument results in a torque about multiple joints. Any force applied to the surgical instrument parallel to the plane of the axes 35 and 41 can be sensed by torque sensors $S_1$ and $S_2$. The processor resolves the outputs of the torque sensors $S_1$ and $S_2$ to determine the direction and magnitude of the torque applied to the surgical instrument.

In the case that the wrist 13 is at the distal end of a surgical instrument, then forces applied to the end effector 53 are detectable as described with respect to the surgical instrument in the preceding paragraph.

Each joint of the robot arm of FIG. 3 can be driven independently of the other joints by one or more motive devices such as electric motors or hydraulic pistons. The motive device(s) could be located locally at the respective joint, or it/they could be located closer to the base of the robot and coupled to the joints by couplings such as cables or linkages. The motive devices are controllable by a user of the robot. The user could control the motive devices in real time by one or more artificial input devices, such as joysticks, or by inputs derived from sensors acting on a master arm that is moved by the user. Alternatively, the motive devices could be controlled automatically by a computer that has been pre-programmed to perform a surgical procedure. The computer could be capable of reading a computer-readable memory that stores a non-volatile program executable by the computer to cause the robot arm to perform one or more surgical procedures.

Figure 7:
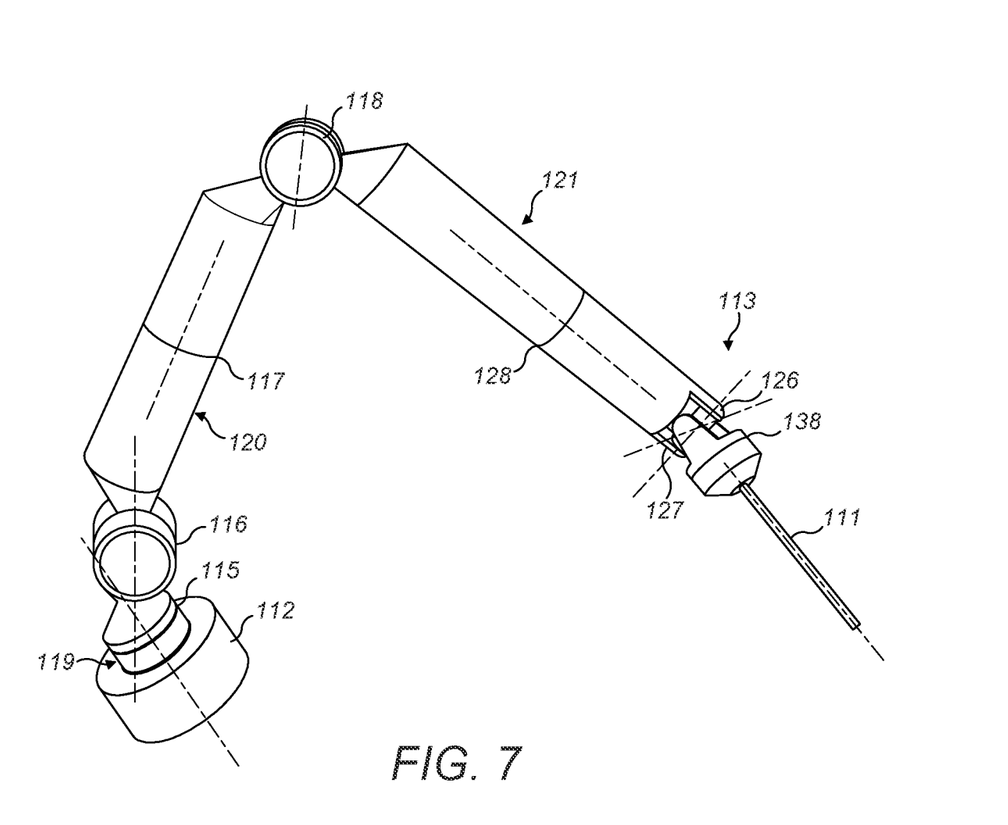
FIG. 7 shows an alternative design of a robot arm.

FIG. 7 shows an alternative design of surgical arm. The arm of FIG. 7 comprises a base 112, four joints 115, 116, 117, 118, three shaft sections 119, 120, 121 and a wrist unit 113. The joints are revolute joints. The shaft sections are rigid, with the exception of joints 115 and 117. A surgical instrument 111 is attached to the terminal part of the wrist unit.

The first shaft section 119 extends from the base 112 and comprises joint 115. The first shaft section 119 is attached to the second shaft section 120 by joint 116. The second shaft section 120 comprises joint 117. The second shaft section is attached to the third shaft section 121 by joint 118. The third shaft section 121 terminates in a revolute joint 128 whereby it is attached to the wrist unit 113. The wrist unit comprises an intermediate pair of revolute joints 126, 127, which together constitute a universal joint, and a terminal revolute joint 138.

As with the analogous joints in the robot arm of FIG. 3, the axes of each of the following pairs of joints may independently be transverse to each other, substantially orthogonal to each other (e.g. within any of 30°, 20° or 10° of being orthogonal) or orthogonal to each other: 115 and 116, 116 and 117, 117 and 118, 118 and 128, 128 and 126, 128 and 127, 126 and 138, 127 and 138, 126 and 127. As with the analogous joints in the robot arm of FIG. 3, the axes of the following joints may independently be aligned with (e.g. within any of 30°, 20° or 10° of) or parallel with the principal axis of elongation of the shaft in or on which they are set: joint 117 (with shaft section 120), joint 128 (with shaft section 121). As with the analogous joints in the robot arm of FIG. 3, the wrist may be configured such that the axes of joints 128 and 138 can in one or more configurations of the arm be aligned. Conveniently that alignment may happen when the wrist is in the mid-range of its side-to-side movement. As with the analogous joints in the robot arm of FIG. 3, conveniently the axis of elongation of the instrument 111 may be aligned with (e.g. within any of 30°, 20° or 10° of) or parallel with the axis of joint 138. The axis of elongation of the instrument may be coincident with the axis of joint 138.

The robot arm of FIG. 7 differs from that of FIG. 3 in that the arm sections 119, 120, 121 are configured so that the axis of joint 116 has a substantial lateral offset from the axes of joints 115 and 117 and so that the axis of joint 118 has a substantial lateral offset from the axes of joints 116 and 118. Each of those offsets may independently be, for example, greater than 50 mm, 80 mm or 100 mm. This arrangement is advantageous in that it increases the mobility of the arm without increasing the swept volume close to the tip of the instrument.

In the robot arm of FIG. 7 the axis of the revolute joint closest to the base (joint 115) is fixed at a substantial offset from vertical, e.g. by at least 30°. This may be achieved by fixing the base in an appropriate orientation. If the arm is set up so that the axis of joint 115 is directed generally away from the end effector, as illustrated in FIG. 7, this reduces the chance of a kinematic singularity between joint 115 and joint 117 during an operation.

Thus the arm of FIG. 7 has a number of general properties that can be advantageous in a surgical robot arm.

It comprises a series of revolute joints along its length that include a series of four joints in order along the arm that alternate between (a) having an axis that runs generally towards the next joint in the sequence (a "roll joint") and (b) having an axis that runs generally transverse to the axis of the next joint in the sequence (a "pitch joint"). Thus the arm of FIG. 7 includes roll joints 115 and 117 and pitch joints 116 and 118. This series of joints can provide the arm with a high degree of mobility without the arm needing to be heavy or bulky or to comprise an excessive number of joints. As indicated above, alternate joints can usefully be offset laterally from each other.

It comprises a wrist section commencing at a roll joint (128) and having two pitch joints (126, 127). The pitch joints of the wrist can be co-located such that their axes intersect in all configurations of the arm. This series of joints can provide the end effector with a high degree of mobility about the end of the arm.

A wrist section that terminates in a revolute joint (138) whose axis is coincident with the axis of extension of the surgical instrument. Most conveniently the instrument shaft is elongated linearly and the axis of that joint is aligned with the shaft. This arrangement can permit the end effector to be readily rotated to a desired orientation through motion at a single joint without excessively disrupting a wound channel in the patient. Without this arrangement, the arm joints would have to be controlled to move together to achieve rotation of the instrument shaft about its own axis. This would require the workspace of an elbow joint of the arm to be increased to enable it to swing across its range of motion to achieve the desired motion of the instrument. Large joint workspaces are undesirable for the operating theatre staff who work around the robot arm. This arrangement can also reduce the need for a joint performing an equivalent function in the instrument itself.

A proximal revolute joint (115) that is substantially offset from vertical and most conveniently directed away from the site of the operation in the patient. This reduces the chance of that joint having a kinematic singularity with another joint of the arm.

As discussed above, the proximal series of joints in the arms of FIGS. 3 and 7 in order towards the distal end of the arm are, using the terms defined above, roll, pitch, roll and pitch joints. This series of joints may be denoted RPRP, where "R" denotes a roll joint, "P" denotes a pitch joint and the joints are listed in series from the proximal towards the distal end of the arm. Using the same terminology, other convenient joint sequences for surgical arms include the following:

1. PRPRP: i.e. the joint sequence of the robot arm of FIGS. 3 and 7 but with an additional pitch joint between the RPRP joint sequence and the base.
2. RPRPR: i.e. the joint sequence of the robot arm of FIGS. 3 and 7 but with an additional roll joint between the RPRP joint sequence and the wrist.
3. RPRPRP: i.e. a series of three RP pairs in succession, akin to the joint sequence of the robot arm of FIGS. 3 and 7 but with an additional pitch joint between the RPRP joint sequence and the base and an additional roll joint between the RPRP joint sequence and the wrist.

Further joints could be added to the arm.

Each of these arms could have a wrist of the type shown in FIG. 3 or 7. One of the joints 28, 38 could be omitted from the wrist.

Figure 5:
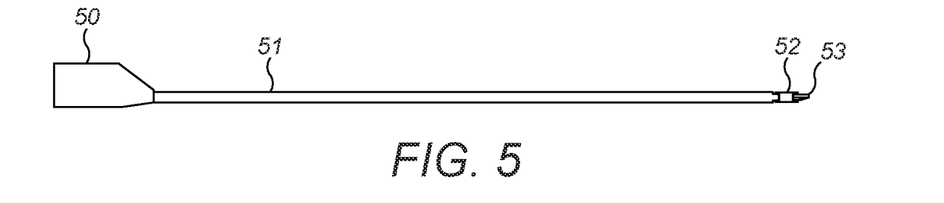
FIG. 5 shows a surgical instrument.

As indicated above, the surgical instrument of FIG. 5 may have one or more joints 52 near its tip. If the robot arm is of the type described herein then the surgical instrument may conveniently include only two joints. They can conveniently be revolute joints whose axes run transversely to the instrument shaft 51. The axes of those joints could intersect, forming a universal joint, or could be offset in the direction of elongation of the instrument shaft. The joints of the instrument could be driven by motive means in the arm, and the motion transmitted to the joints through cables or linkages in the instrument. The connector in the terminal part of the wrist unit and the instrument base 50 may be configured to provide for transmitting such motion into the instrument. Conveniently the joints on the instrument do not include a revolute joint whose axis is aligned with the shaft of the instrument. The motion that would be provided by such a joint can conveniently be served by the joint 38 on the wrist of the robot arm. In many surgical procedures such motion is not needed. The instruments are often intended to be disposable; therefore cost can be reduced by omitting such a joint from the instrument. Omitting such a joint also simplifies the mechanical interaction needed between the instrument and the arm since motion for that joint need not be transmitted into the instrument.

The torque sensors may be sensors that are in direct contact with the wrist. For example, a resistance-based strain gauge may be used as a torque sensor. This is connected directly to the portion of the wrist being rotated. As torque is applied about the axis of rotation, the strain gauge deforms changing its resistance. This resistance change is measured, for example by a bridge circuit and output to the processor of the control unit. The processor determines the torque applied about the axis to be a function of the resistance change.

As another example, a piezoelectric strain gauge may be used as a torque sensor. Again, this is connected directly to the portion of the wrist being rotated. The gauge is made of a piezoelectric material which generates a voltage across it when strained. As torque is applied about the axis of rotation, the piezoelectric strain gauge is deformed, generating a voltage across it which is measured and output to the processor of the control unit. The processor determines the torque applied about the axis to be a function of the voltage change.

The torque sensors may be sensors which are not in direct contact with the wrist. For example, a magnetostrictive-based gauge may be used as a torque sensor. Magnetostrictive material is deposited on the portion of the wrist being rotated. As torque is applied about the axis of rotation, external flux is generated by the magnetostrictive material being stressed. Sensors positioned in close proximity to the magnetostrictive material, but not in contact with the joint which is moving, pick up the current generated and output it to the processor of the control unit. The processor determines the torque applied about the axis to be a function of the generated current.

The output of the torque sensors may be passed to the control unit by signals passing through wires attached externally to the casing of the robot body. Alternatively, the wires may pass internally down the cores of shafts of the robot arm to the control unit. Alternatively, the torque sensors and the control unit may be capable of wireless communications. In this case, the outputs of the torque sensors are transmitted wirelessly by the torque sensors to the control unit.

The control unit may implement a force feedback mechanism to convert the sensed torque about the joints of the wrist into force feedback to the surgeon. For example, haptic technology may be used to convert the sensed torques into physical sensations in the input devices that the surgeon interacts with.

In operational use, the robot arm of FIG. 3 could be covered by a sterile drape to keep the arm separated or sealed from the patient. This can avoid the need to sterilise the arm before surgery. In contrast, the instrument would be exposed on the patient's side of the drape: either as a result of it extending through a seal in the drape or as a result of the drape being sandwiched between the connector in the terminal part of the wrist unit and the instrument base 50. Once the instrument has been attached to the arm it can be used to perform an operation. In performing an operation the arm can first be manipulated so that the axis of the instrument shaft 51 is aligned with the axis between a desired entry point on the exterior of the patient (e.g. an incision in the patient's skin) and the desired operation site. Then the robot arm can be manipulated to insert the instrument through the incision and onwards in a direction parallel to the axis of the instrument shaft until the end effector reaches the operation site. Other tools can be inserted in a similar way by other robot arms. Once the required tools are at the operation site the operation can be conducted, the tools can be withdrawn from the patient's body and the incision(s) can be closed, e.g. by suturing. If it is desired to move the end effector in a direction transverse to the axis of the instrument shaft when the instrument is located in the patient, such motion is preferably performed by rotating the instrument shaft about a centre of motion located at the incision through which the instrument is passing. This avoids making the incision bigger.

A robot arm of the type described above can provide a range of advantages for performing surgical procedures. First, because it does not include an excessive number of joints whist still providing the range of motion needed to position the instrument as a whole and particularly the end effector of the instrument in a wide range of locations and orientations the robot arm can be relatively slim and lightweight. This can reduce the chance of a human being injured through undesirable motion of the arm, e.g. when nurses are working around the arm when an operating theatre is being set up to receive a patient. It can also improve the accessibility of multiple such arms to an operation site, especially a site for a procedure such as an ENT (ear, nose and throat) procedure where typically multiple instruments must access the operation site through a small opening. Similar considerations arise in, for example, abdominal procedures where it is common for multiple instruments to enter the patient from a region near the umbilicus and to extend internally of the ribcage into the abdomen of the patient; and in procedures in the pelvic area where the direction in which instruments can approach the operation site is limited by the need to avoid the pelvic bone and other internal structures. Similarly, an arm having improved range of motion can make it easier to position the bases of multiple robots around an operating site because surgical staff have more freedom over where to locate the robot bases. This can help to avoid the need to redesign existing operating room workflows to accommodate a robot. Second, the arm provides sufficient redundant motion that surgical staff have flexibility in positioning the base of the robot relative to the patient. This is important if multiple robots need to work at a small surgical site, if there is additional equipment in the operating theatre or if the patient is of an unusual dimension. Third, when the wrist section comprises a roll joint located proximally of a pair of crossed-axis pitch joints, as in FIGS. 4a, 4b, and 4c, and particularly if in addition the arm and the instrument are configured so that the instrument shaft extends directly away from those pitch joints, then the motion of the wrist is close to that of a human, making it easier to translate conventional surgical procedures so that they can be performed by the robot. This relationship between the wrist and the instrument also assists in enabling multiple arms to closely approach each other near a surgical site since the terminal sections of the main arm members (e.g. 21 and 121) can be angled relative to the instrument shaft without compromising the freedom of motion of the instrument shaft. This is in part because when the end effector needs to be moved within the patient by rotation about a centre located at the external point of entry of the instrument shaft into the patient, that rotation can be provided exclusively by the wrist, without being hindered by kinematic singularities or complex interactions between multiple joints having spatially offset axes, whilst the remainder of the arm merely translates the wrist to the required location. When the robot is under computer control the program for the computer may be defined so as to cause the robot to translate the location of the end effector by rotation of the end effector about a point along the shaft of the instrument. That point may be coincident with or distal of the incision into the patient. The program may be such as to achieve the said translation of the end effector by commanding the motive driver(s) for the wrist to cause joints 26 and/or 27 to rotate the instrument about the point and by simultaneously commanding the motive driver(s) for the remainder of the arm to cause the wrist to translate.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A surgical robotic component comprising an articulated terminal portion, the terminal portion comprising:
   a distal segment having an attachment for an instrument to be connected thereto, wherein the attachment is fixed relative to the distal segment such that it maintains a fixed relative orientation between the distal segment and the instrument;
   an intermediate segment;
   a basal segment;
   a first articulation between the distal segment and the intermediate segment, the first articulation permitting relative rotation of the distal segment and the intermediate segment about a first axis; and
   a second articulation between the intermediate segment and the basal segment, the second articulation permitting relative rotation of the intermediate segment and the basal segment about a second axis,
   wherein:
   the intermediate segment comprises a third articulation permitting relative rotation of the distal segment and the basal segment about third and fourth axes; and
   the first, second and third articulations are arranged such that in at least one configuration of the third articulation:
   the first and second axes are collinear;
   the third and fourth axes are transverse to the first axis;
   the third and fourth axes are transverse to each other;
   the third and fourth axes intersect each other; and
   the surgical robotic component is configured to determine torque about the third and fourth axes.

2. A surgical robotic component as claimed in claim 1, the terminal portion being attached to the remainder of the surgical robotic component by the basal segment.

3. A surgical robotic component as claimed in claim 2, wherein the attachment is only articulable relative to the basal segment by the first, second and third articulations.

4. A surgical robotic component as claimed in claim 2, wherein the attachment is located on the first axis.

5. A surgical robotic component as claimed in claim 2, the surgical robotic component being located at the end of a surgical robot arm, and further comprising a surgical instrument attached to the attachment.

6. A surgical robotic component as claimed in claim 5, wherein the surgical instrument extends in a direction along the first axis.

7. A surgical robotic component as claimed in claim 2, the surgical robotic component being located at the end of a surgical instrument, and further comprising a surgical end effector attached to the attachment.

8. A surgical robotic component as claimed in claim 7, wherein the surgical end effector extends in a direction along the first axis.

9. A surgical robotic component as claimed in claim 1, the intermediate segment comprising a first torque sensor configured to sense torque about the third axis.

10. A surgical robotic component as claimed in claim 1, the intermediate segment comprising a second torque sensor configured to sense torque about the fourth axis.

11. A surgical robotic component as claimed in claim 1, the terminal portion further comprising a third torque sensor configured to sense torque about the first axis.

12. A surgical robotic component as claimed in claim 1, the terminal portion further comprising a fourth torque sensor configured to sense torque about the second axis.

13. A surgical robotic component as claimed in claim 1, wherein in the said configuration the third and fourth axes are perpendicular to each other.

14. A surgical robotic component as claimed in claim 1, wherein in the said configuration the third and fourth axes are perpendicular to the first axis.

15. A surgical robotic component as claimed in claim 1, wherein the first articulation is a revolute joint.

16. A surgical robotic component as claimed in claim 1, wherein the second articulation is a revolute joint.

17. A surgical robotic component as claimed in claim 1, wherein the third articulation is a spherical joint or a pair of revolute joints.

18. A surgical robotic component as claimed in claim 17, wherein the third articulation is a universal joint.

* * * * *